US 8,927,896 B2

(12) United States Patent
Kuo

(10) Patent No.: US 8,927,896 B2
(45) Date of Patent: Jan. 6, 2015

(54) BATTERY POWERED HANDHELD AIR PLASMA SPRAY

(71) Applicant: Spencer P. Kuo, River Edge, NJ (US)

(72) Inventor: Spencer P. Kuo, River Edge, NJ (US)

(73) Assignee: Adventix Technologies, Inc., River Edge, NJ (US)

( * ) Notice: Subject to any disclaimer, the term of this patent is extended or adjusted under 35 U.S.C. 154(b) by 0 days.

(21) Appl. No.: 14/053,619

(22) Filed: Oct. 15, 2013

(65) Prior Publication Data

US 2014/0180276 A1    Jun. 26, 2014

(51) Int. Cl.
*B23K 9/00* (2006.01)
*B23K 9/02* (2006.01)
*A61B 18/04* (2006.01)
*H05H 1/50* (2006.01)
*A61B 18/12* (2006.01)

(52) U.S. Cl.
CPC .............. *A61B 18/042* (2013.01); *H05H 1/50* (2013.01); *A61B 2018/1226* (2013.01); *H05H 2245/1225* (2013.01)
USPC ................ 219/121.47; 606/49; 219/121.48; 219/121.52

(58) Field of Classification Search
USPC ............. 219/121.52, 121.48, 121.59, 121.47
See application file for complete search history.

(56) References Cited

U.S. PATENT DOCUMENTS

| 3,576,422 | A  | * | 4/1971  | Beaupre et al. | ............ 219/130.4 |
| 4,904,903 | A  | * | 2/1990  | Pacholok | .................. 315/209 R |
| 5,538,765 | A  | * | 7/1996  | Kurihara et al. | .............. 427/577 |
| 5,977,715 | A  | * | 11/1999 | Li et al. | ..................... 315/111.51 |
| 6,455,808 | B1 | * | 9/2002  | Chung et al. | ............. 219/130.51 |
| 7,742,167 | B2 | * | 6/2010  | Morrisroe | ..................... 356/316 |
| 7,777,151 | B2 | * | 8/2010  | Kuo | ........................ 219/121.47 |
| 8,005,548 | B2 | * | 8/2011  | Watson | ......................... 607/101 |
| 8,063,339 | B2 | * | 11/2011 | Paquette | .................... 219/130.4 |
| 8,111,498 | B2 | * | 2/2012  | Ben-Yaakov | ................. 361/232 |

* cited by examiner

*Primary Examiner* — Matthew F Desanto

(57) ABSTRACT

A battery powered handheld air plasma spray was designed, developed and successfully demonstrated. The power supply includes a battery, a dc HID ballast and a series LC matching circuit. This matching circuit is designed to maintain the performance of the HID ballast while driving arc discharges, which are rotated around the electrodes by the magnetic field of a ring magnet. The produced plasma is in a non-equilibrium state; thus, the plasma effluent is low temperature (touchable) and yet carries abundant reactive atomic oxygen, which can rapidly activate blood coagulation processes and can effectively kill numerous microbes. This invention is for blood coagulation and sterilization applications. The device may be installed in vehicles and carried and operated in open fields without AC power sources. It may be used for bleeding control in a serious mishap to treat wounds without having to move the injured.

2 Claims, 4 Drawing Sheets

BATTERY POWERED HANDHELD AIR PLASMA SPRAY

§1. BACKGROUND OF THE INVENTION

§1.1 Field of the Invention

This invention concerns the design of a battery powered, handheld air plasma spray for blood coagulation and sterilization applications.

§1.2 Background

Bleeding, even from an external hemorrhage, may be life threatening if it is not treated swiftly (See, e.g., the article: P. Jevon and L. Cooper, "First aid. Part 5. First-aid treatment for severe bleeding," *Nursing Times,* 104, 26-27, 2005 (hereafter referred to as "the Jevon article")). Most cases of bleeding occur under emergency situations. The treatment has to repair the cause of bleeding, relieve symptoms, and prevent complications. Thus, new methods and devices which can effectively stop bleeding are significant, and can help to save the life of an injured person, especially in battlefield situations (See, e.g., the article: USA Today, "Advanced first aid for troops sought," A1, 14 Sep. 2009 (hereafter referred to as "the USA Today article")).

Non-thermal atmospheric pressure air plasma can clot blood for bleeding control (See, e.g., the article: Spencer Kuo, "Air plasma for medical applications," *J. Biomed. Sci. Eng.* (*JBiSE*), 5, 481-495, 2012 (hereafter referred to as "the Kuo article"). However, the present plasma devices designed for blood coagulation applications employ an AC source (e.g., 110V/60 Hz or 220V/50 Hz) for their operation, thus, these present devices are not useful for certain emergency situations.

A torch module described in the U.S. Pat. No. 7,777,151 B2 titled "Portable Plasma Sterilizer," ("the '151 patent") can be run in low frequency (e.g., 60 Hz) periodic mode to produce low temperature non-equilibrium air plasma. Based on the principle of this torch module, a battery powered handheld air plasma spray was designed, developed and successfully demonstrated. One of the applications is for blood bleeding control and the other is for sterilizing contaminated objects. The invention is lightweight, portable, and a handheld battery powered device, making the device easy to carry to the site of a serious mishap to treat wounds without having to move the injured.

§2. SUMMARY OF THE INVENTION

A battery powered handheld air plasma spray device was designed and developed. A photo of the device including the power supply is shown in FIG. 1. The produced plasma jet, shown in the insert of FIG. 1, carries abundant reactive atomic oxygen (RAO) which can effectively activate erythrocyte-platelet interactions, for stopping blood bleeding from external wounds (See, e.g., the Kuo article) and kill numerous microbes (See, e.g., the article: Spencer P. Kuo, "Plasma Assisted Decontamination of Bacterial Spores", *The Open Biomedical Engineering J.*, 2, 36-42, 2008 (hereafter referred to as "the Spencer article")). A schematic of the torch design is presented in FIG. 2.

A block diagram of the power supply of the present invention is shown in FIG. 3. The power supply includes a dc high-intensity-discharge (HID) ballast and a series LC matching circuit. The HID ballast is adaptable to a number of dc power sources, such as a 12V car battery or a 14-18V power tool battery and can deliver up to 550 V output voltage. Moreover, when the output voltage reaches 500-550 V, the insulated-gate bipolar transistor (IGBT) conducts to set off the capacitor in the ignition circuit of the HID ballast that generates voltage spikes of 2.5 kV-3 kV for activating the discharge in the plasma spray generator. Because the voltage drops significantly in the arc discharge, it represents a dynamic load on the HID ballast; thus a matching circuit is needed to compensate for the dynamic variation of the discharge voltage and current in order to maintain the performance of the HID ballast.

An example of operating the device powered by a 12V battery jump starter is shown in FIG. 4; the example simulates the operation of the device powered by a 12V cigarette lighter, commonly found in automobiles and trucks.

§3. BRIEF DESCRIPTION OF THE DRAWINGS

FIG. 1 is a photo of the complete system of the invention showing a handheld plasma Spray generator connected to an air pump in a box through a flexible air tube as well as connected electrically to the output terminals of its power supply in the same box through a pair of electric wires inside the same air tube. A series LC matching circuit connected in parallel with the plasma spray generator is also placed in the box. The insert is a photo of an operating air plasma spray.

§4. DETAILED DESCRIPTION

The present invention involves a novel design of a low temperature air plasma spray generator, which is handheld, uses only ambient airflow, produces RAO in the plasma effluent, is battery powered and portable. The following description is presented to enable a skilled tradesman to fabricate and use the invention in the context of a particular requirement and associated application. Various modifications to the disclosed device will be apparent to skilled tradesmen, and the general principles set forth below may be applied to other devices and applications. Thus, the present invention is not intended to be limited to the device as shown.

In the following, functions, which may be performed by the present invention, are presented in §4.1. Then, details of aa device built in accordance with the present invention is described in §4.2. Several applications of the invention are described in §4.3. Thereafter, operations of the apparatus are described in §4.4. Finally, conclusions regarding the present invention are presented in §4.5.

§4.1 Functions

The present invention may be used to generate an air plasma jet carrying RAO in open air. The generator is handheld and is steered freely to spray the produced plasma effluent over a large volume or area. The plasma effluent is low temperature and touchable; the present invention does not rely on the thermal effect for blood coagulation and sterilization applications. It is safe to have a close contact of the device's emitted plasma spray with objects such as skin, clothes, and paper.

§4.2 Structures

In the following, a portable handheld air plasma spray is described.

Figure 1:
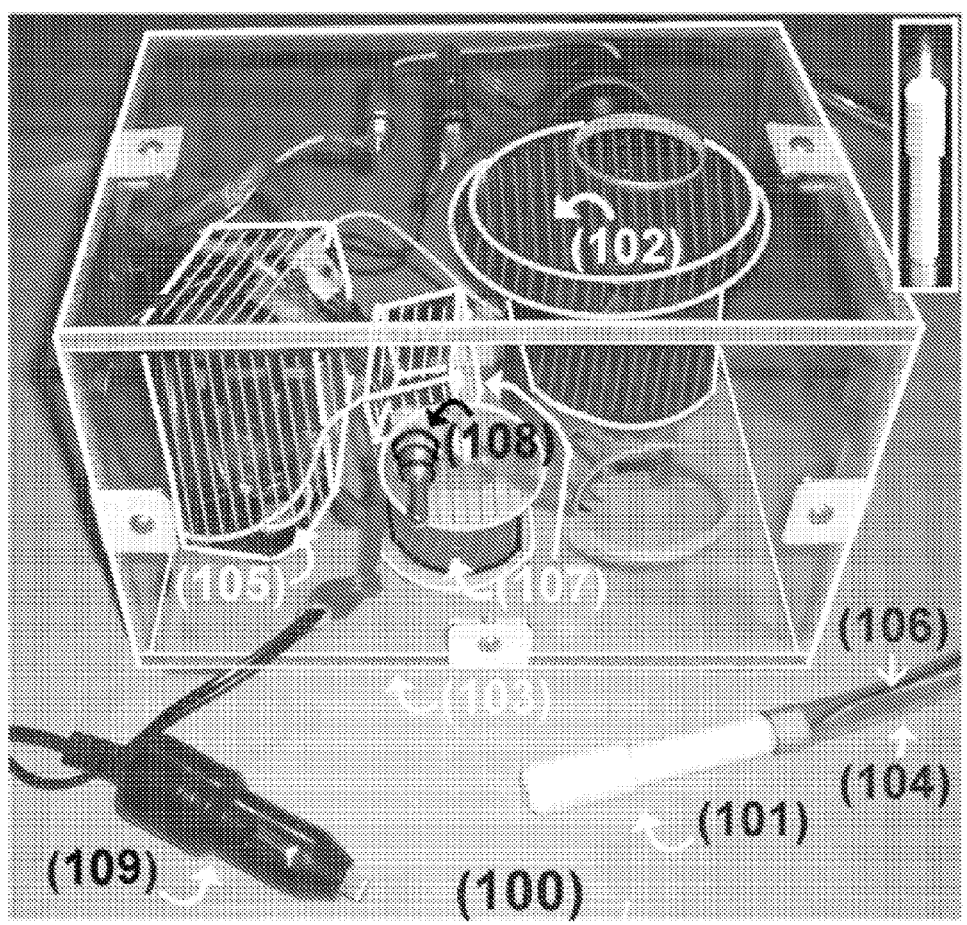

The device (100), as shown by the photo presented in FIG. 1, consists of a handheld air plasma spray generator (101) which is connected to an air pump (102) placed in a box (103)

through a flexible air tube (104). The electric terminals of the generator are connected to the output terminals of the power supply (105) also placed inside the box (103) through two electric wires (106) placed inside the flexible air tube (104). A series LC matching circuit (107) also placed inside the box (103) is connected in parallel with the plasma spray generator (101) to compensate for the dynamic variation of the plasma impedance in the discharge. A toggle switch (108) mounted on a wall of the box (103) is used to control the on-off of the plasma generator (101). A dc plug (109) is used for connecting the device to battery power sources.

Figure 2:
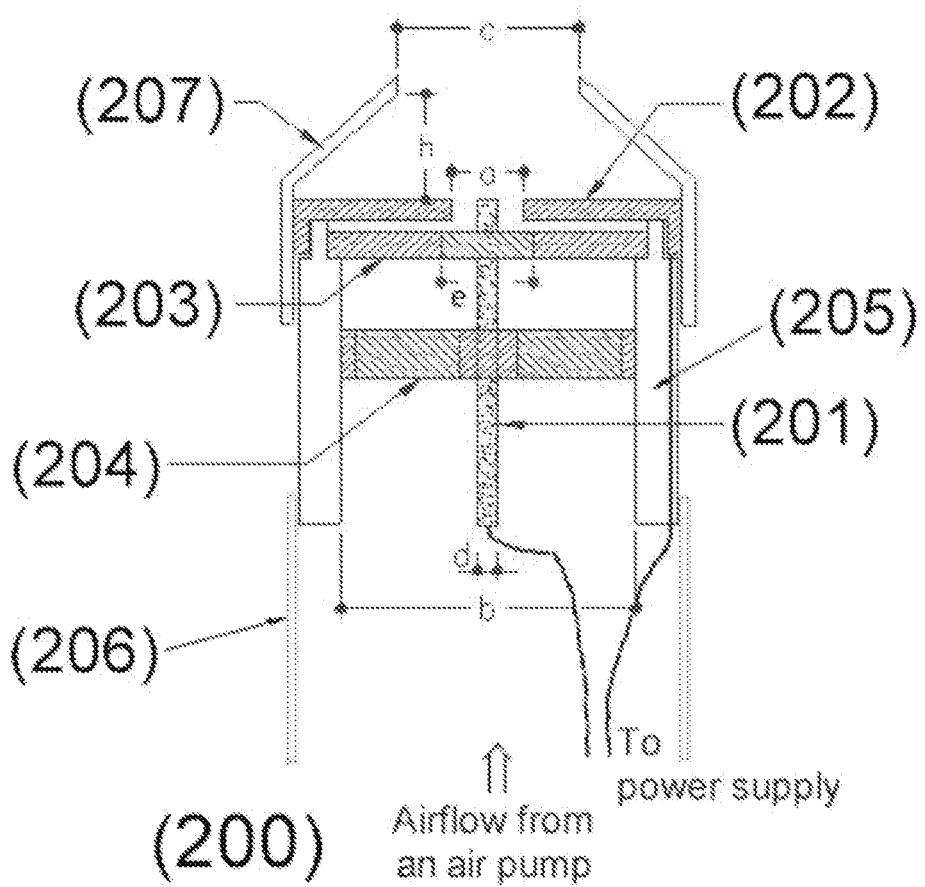
FIG. 2 is a schematic of the plasma spray generator.

This plasma spray generator, as shown by the schematic (200) in FIG. 2, consists of a pair of concentric electrodes (201, 202), a ring magnet (203), and a position holder (204). This ring magnet (203) is inserted through the central electrode (201) [a cylindrical tungsten (or copper) rod with a diameter "d"] and held inside the outer electrode (202) of the plasma spray generator as illustrated in FIG. 2. The magnetic field B of the permanent magnet introduces a Lorentz force density $F=J\times B$ on the discharge current density J; the Lorentz forces rotates the discharge around the central electrode (201) so that the undesirable arc constriction can be minimized and the erosion of the electrodes by the discharges is reduced. It also stabilizes the discharge, keeps the plasma in the non-equilibrium state with low thermal temperature, and increases the plasma volume.

A position holder (204) tie fit with the central electrode (201) keeps the central electrode (201) centered on the cylindrical tube (205) axis. This position holder (204), as shown in the insert of FIG. 2, has large pass-through openings for the airflow delivered through a flexible air tube (206) from an air pump (102), shown in FIG. 1. The airflow passes through the openings of the position holder (204) to the gap between the electrodes.

A cap (207) is introduced to direct the flow of the plasma effluent as well as to cover the electrodes for the safety purposes so that the high voltage (HV) central electrode is not exposed.

The dimensions "a" of the inner diameter of the outer electrode (202), "b" of the inner diameter of the cylindrical tube (205), "c" of the opening diameter of the cap (207), "d" of the diameter of the central electrode (201), "e" of the inner diameter of the ring magnet (203), and "h" of the height of the cap (207), are variable, with the exception that e>a is required in order to avoid the undesirable discharge between the central electrode (201) and the ring magnet (203) and c>a is preferred. The outer shape of the cylindrical tube (205) is arbitrary.

Figure 3:
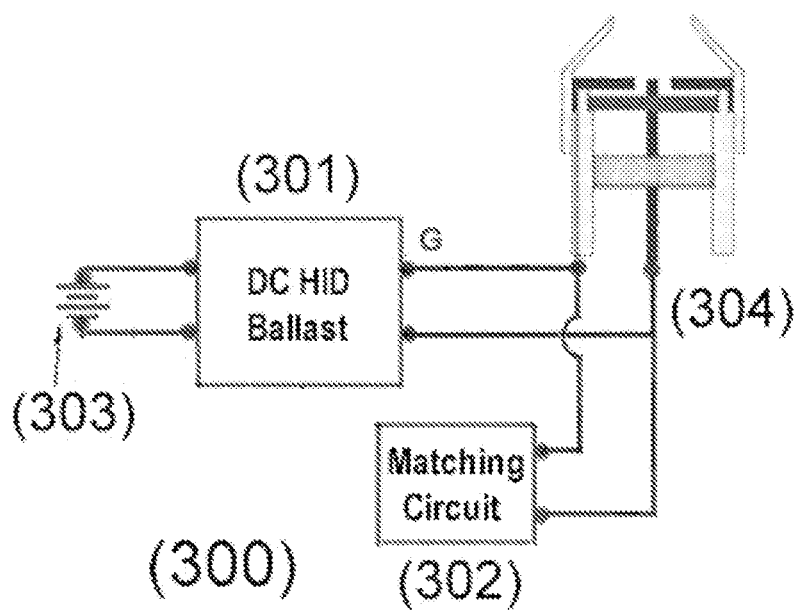
FIG. 3 is a block diagram of the power supply including a battery, a dc HID ballast and a matching circuit; the output connection is also shown.

Shown in FIG. 3 is a block diagram of a power supply (300), which consists of a dc HID ballast (301), a matching circuit (302) and battery (303). The dc HID ballast (301) converts the dc input voltage (e.g., 12 to 18V) from the battery (303) up to 550 V output. It also contains an ignition circuit which generates voltage spikes of 2.5-3 kV when the output voltage of the HID ballast reaches 500-550 V. The 2.5-3 kV voltage spikes trigger air breakdown to set off the subsequent discharge by the 500-550V output of the HID ballast. A series LC matching circuit (302) is connected in parallel with the plasma spray generator (304). The arc discharge in the plasma spray generator (304) is a dynamic load of the HID; thus this matching circuit (302) is needed to compensate for the dynamic variation of the load impedance in order to maintain the performance of the HID ballast.

Figure 4:
FIG. 4 is an example of operating the plasma spray generator with a 12V battery jump starter. The inset shows that the plasma plume is touchable.

FIG. 4 shows that the invention is a battery-powered device. In the photo, a 12V battery jump starter (401) is used to simulate the electric charger of an automobile or truck cigarette lighter. A plasma plume emitted from the cap of the plasma spray generator (402) is shown. The inset in FIG. 4 demonstrates that the plasma plume is touchable.

§4.3 Applications of the Device

A device made in accordance with the present invention, such as that described in §4.2, may be used as a plasma spray carrying reactive species such as atomic oxygen.

§4.3.1 Blood Coagulation

As verified by tests in-vivo, air plasma can rapidly clot blood and accelerate wound healing (See e.g., the Kuo article) through RAO as the catalyst in the coagulation processes. The invented device produces non-equilibrium air plasma, which has a lower thermal temperature and higher electron excitation temperature than that generated by the device described in "the '151 patent", thus, this device produces denser RAO in its plasma effluent. This device may be installed in vehicles and ambulances, and carried in battlefields and open fields such as camping areas and parks. It may be used for bleeding control in emergency situations. The plasma effluent also sterilizes wounds and helps to heal wounds simultaneously. This dry sterilizing approach is particularly suitable for wounds, for example, caused by burning. Adding an AC to DC adapter, this device may be used at home for first aid.

§4.3.2 Sterilization

The present invention device is portable, fast working, and operates stably with ambient air discharge (i.e., there is no mass storage needed for its operation). The produced plasma can be sprayed easily. This air plasma spray may be used to kill microbes on clothes, handles, as well as to decontaminate instruments and filters.

This device is based on non-thermal and dry approach for sterilization and decontamination; the process is "green" (i.e., no hazardous chemicals are employed or released) as well as safe to personnel (short lifetime of RAO) and sensitive equipment. These are advantageous features for sterilization and decontamination applications.

§4.4 Operations of an Exemplary Embodiment

An exemplary air plasma spray, such as described in §4.2 above, is battery powered. The battery powered dc HID ballast may be used as the power supply, but a matching circuit is needed to maintain the performance of the HID ballast. A power supply having its block diagram shown in FIG. 3 may be used to operate the air plasma spray.

§4.5 Conclusions

The invented air plasma spray is handheld, employs a dc input, such as from a battery, and needs only ambient airflow. The plasma effluent produced by the invention rapidly clots blood, kills microbes, and is low temperature safe for personnel and sensitive instruments. This is a practical device to be used for first aid as for example, in vehicles and open fields, as well as in industrial and household settings.

Such a handheld air plasma spray may be fabricated from commercially available parts together with the custom designed components described in §4.2.

What is claimed is:

1. A battery powered handheld air plasma spray using ambient air as the working gas, said air plasma spray comprising:
   a pair of concentric electrodes, said electrodes consisting of a cylindrical rod-shaped inner electrode and a ring-shaped outer electrode;
   a ring-shaped permanent magnet placed upstream of the electrode ends and concentric with and around the inner electrode, permitting airflow between the electrode downstream ends;
   a position holder securing said inner electrode to be aligned axially with said outer electrode, said holder positioned upstream of the electrode ends and said ring-shaped magnet at a distance to allow air flow through the openings of said holder to the downstream ends of said electrodes to the discharge gap without being blocked by the ring magnet;

a tube frame housing, said electrodes, ring-shaped magnet and position holder contained within said housing having an inlet end and an outlet end;

a cap attached to the outlet end of the tube frame housing, said cap positioned downstream of the discharge ends of said electrodes for protecting the discharge ends of the electrodes;

an air pump, said pump supplying air flow to the electrode discharge gap through a flexible air tube attached to the inlet end of said housing;

a dc high-intensity-discharge (HID) ballast, said ballast providing high voltage spikes for triggering air breakdown and also providing the discharge voltage to said electrodes;

an ignition circuit which generates voltage spikes of 2.5-3 kV; and a series LC matching circuit, said matching circuit connected in parallel with said electrodes.

2. The apparatus of claim 1 is operated by a dc power source of output voltage of 12 to 18 $V_{DC}$.

* * * * *